United States Patent
Tralshawala et al.

(10) Patent No.: US 10,018,596 B2
(45) Date of Patent: Jul. 10, 2018

(54) SYSTEM AND METHOD FOR MONITORING COMPONENT HEALTH USING RESONANCE

(71) Applicant: General Electric Company, Schenectady, NY (US)

(72) Inventors: Nilesh Tralshawala, Rexford, NY (US); Prashanth D'Souza, Bangalore (IN); Ravi Yoganatha Babu, Bangalore (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 239 days.

(21) Appl. No.: 15/061,505

(22) Filed: Mar. 4, 2016

(65) Prior Publication Data

US 2017/0254783 A1  Sep. 7, 2017

(51) Int. Cl.
*G01N 29/14* (2006.01)

(52) U.S. Cl.
CPC ....... *G01N 29/14* (2013.01); *G01N 2291/044* (2013.01)

(58) Field of Classification Search
CPC .................. G01N 29/14; G01N 2291/044
USPC .......................................................... 73/587
See application file for complete search history.

(56) References Cited

U.S. PATENT DOCUMENTS

| | | | |
|---|---|---|---|
| 4,089,224 A * | 5/1978 | Scott | G01N 3/06 73/587 |
| 4,372,163 A | 2/1983 | Tittmann et al. | |
| 4,603,584 A | 8/1986 | Bartle et al. | |
| 4,685,335 A | 8/1987 | Sato et al. | |
| 5,029,474 A | 7/1991 | Schulze | |
| 5,065,630 A | 11/1991 | Hadcock et al. | |
| 5,152,172 A * | 10/1992 | Leon | G01H 1/006 310/40 R |
| 5,445,027 A * | 8/1995 | Zorner | G01N 29/14 73/593 |
| 5,493,511 A | 2/1996 | Wincheski et al. | |

(Continued)

FOREIGN PATENT DOCUMENTS

| | | |
|---|---|---|
| JP | H0778449 B2 | 8/1995 |
| JP | 2009244090 A | 10/2009 |

OTHER PUBLICATIONS

Acoustic emission monitoring of propulsion systems, Mohamed Nashed, Nov. 2010.*

(Continued)

*Primary Examiner* — J M Saint Surin
(74) *Attorney, Agent, or Firm* — Ernest G. Cusick; Hoffman Warnick LLC (57) ABSTRACT

This disclosure provides systems and methods for using a health monitoring system with acoustic emissions (AE) signals and the resonance frequency of the damage state of a component in a machine to monitor component health. AE signals collected from sensors on an operating machine are analyzed to identify signal features or events that correspond to component resonance frequencies. The AE signal features proximate to the component resonance frequencies and how those features and the component resonance frequency changes over time enable the identification and monitoring of damage states, such as cracks in the stator vanes of a compressor, gas turbine, steam turbine, or generator.

21 Claims, 7 Drawing Sheets

(56) References Cited

U.S. PATENT DOCUMENTS

| | | | |
|---|---|---|---|
| 5,942,690 A * | 8/1999 | Shvetsky | G01N 29/0618 73/593 |
| 6,487,909 B2 | 12/2002 | Harrold et al. | |
| 6,512,379 B2 | 1/2003 | Harrold et al. | |
| 6,668,655 B2 * | 12/2003 | Harrold | F01D 21/045 73/593 |
| 7,062,971 B2 | 6/2006 | Harrold et al. | |
| 7,555,951 B2 * | 7/2009 | Shadman | G01H 1/006 73/579 |
| 8,919,202 B2 | 12/2014 | Keely et al. | |
| 2002/0157471 A1 | 10/2002 | Harold et al. | |
| 2011/0247418 A1 | 10/2011 | Hoyte et al. | |
| 2012/0245860 A1 | 9/2012 | Keely et al. | |
| 2017/0097323 A1 * | 4/2017 | D'Souza | G01N 29/42 |

OTHER PUBLICATIONS

Willsch et al., "New approaches for the monitoring of gas turbine blades and vanes," 2004, pp. 20-23, IEEE Sensors Conference.

\* cited by examiner

SYSTEM AND METHOD FOR MONITORING COMPONENT HEALTH USING RESONANCE

BACKGROUND

The disclosure relates generally to turbomachines, and more particularly, to systems and methods for monitoring health of components, such as stationary blades or stator vanes.

Turbomachines and other complex machines include a large number of mechanical components, including both static and moving components. These components may be subject to stress and wear, particularly in applications and environments that include motion, pressure, and heat. An example of such components are the stator vanes of a gas turbine.

A gas turbine may include an axial compressor at the front, one or more combustors around the middle, and a turbine at the rear. Typically, an axial compressor has a series of stages with each stage comprising a row of rotor blades or airfoils followed by a row of stationary blades or static airfoils, referred to as stator vanes. Accordingly, each stage generally comprises a pair of rotor blades and stator vanes. Typically, the rotor blades increase the kinetic energy of a fluid that enters the axial compressor through an inlet and the stator vanes convert the increased kinetic energy of the fluid into static pressure through diffusion. Accordingly, both sets of airfoils play a vital role in increasing the pressure of the fluid.

Axial compressors incorporating stator vanes are used in a variety of applications, including land based gas turbines, jet engines, high speed ship engines, small scale power stations, or the like. Similar axial compressors may be used in other applications, such as large volume air separation plants, blast furnace air, fluid cracking air, propane dehydrogenation, or other industrial applications.

Moisture, high temperatures, vibration, particulates, chemicals, and other factors in the environment lead to corrosion of various components within a gas turbine or other harsh operating conditions. In combination with operational fatigue in the components, this leads to stress-corrosion cracking. Stress-corrosion cracking can be seen most dramatically in cases of abnormal resonances or impact of foreign objects. Stress and fatigue over time leads to defects and cracks that can then propagate or grow to the point where they present a risk of device failure, such as the liberation of an airfoil and the resulting destruction a large free object wreaks within the device.

Conventional systems and methods exist to monitor the performance and operation of compressors and their airfoils. For example, vibration sensors may be used to monitor vibrations from machines and their components during operations. A change in the frequency or magnitude of existing vibrations may indicate excessive wear and/or crack formation. However, vibration sensors may only detect cracks and other anomalies that are large enough to cause imbalance and vibration in the machine. As a result, vibration sensors may not detect small cracks that do not result in a detectable vibration in a components, such as a stator vane.

Systems using sensing devices configured to detect acoustic emission (AE) signals have also been proposed for machines and components, such as compressors and stator vanes. The AE signals propagate through the machine components and are received by AE sensors. The AE signals are then processed to determine whether signals of interest are present and, if so, used to monitor and validate the health of the components. Improved techniques for identifying and analyzing specific AE signal features corresponding to component health are desirable.

SUMMARY

A first aspect of this disclosure provides systems and methods for using a health monitoring system with acoustic emissions (AE) signals and the resonance frequency of the damage state of a component in a machine to monitor component health. AE signals collected from sensors on an operating machine are analyzed to identify signal features or events that correspond to component resonance frequencies. The AE signal features proximate to the component resonance frequencies and how those features and the component resonance frequency changes over time enable the identification and monitoring of damage states, such as cracks in the stator vanes of a compressor, gas turbine, steam turbine, or generator.

A second aspect of the disclosure provides a system comprising a plurality of sensing devices configured to generate acoustic emission (AE) signals that are representative of acoustic emission waves propagating through at least one component of a machine. The component has a damage state and the damage state has a resonance frequency. The system further comprises a processing subsystem that is in operational communication with the sensing devices to receive AE signals. The processing subsystem includes a resonance detection system that identifies the resonance frequency of the damage state during operation of the machine using the AE signals. The processing subsystem monitors the damage state of the component using the resonance detection system.

A third aspect of the disclosure provides a method of monitoring the health of components of a machine. Acoustic emission (AE) signals are generated that are representative of acoustic emission waves propagating through at least one component of the machine. The component has a damage state and the damage state has a resonance frequency. The resonance frequency of the damage state is identified during operation of the machine using received AE signals. The damage state of the component is monitored using the received AE signals proximate the resonance frequency of the damage state.

A fourth aspect of the disclosure provides a system for monitoring component health of a machine, comprising an acoustic emission (AE) data receiver for receiving AE signals that are representative of acoustic emission waves propagating through at least one component of the machine. The component has a damage state and the damage state has a resonance frequency. The system further comprises a resonance detection system for identifying the resonance frequency of the damage state during operation of the machine using the AE signals. The system still further comprises a health response system for monitoring the damage state of the component using the AE signals proximate the resonance frequency of the damage state.

The illustrative aspects of the present disclosure are arranged to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which.

It is noted that the drawings of the disclosure are not to scale. The drawings are intended to depict only typical aspects of the disclosure, and therefore should not be considered as limiting the scope of the disclosure. In the drawings, like numbering represents like elements between the drawings.

DETAILED DESCRIPTION

As indicated above, the disclosure provides systems and methods for using a health monitoring system with acoustic emissions (AE) signals and the resonance frequency of the damage state of a component in a machine to monitor component health. During normal service conditions, cracks occur in weakening machine components due to corrosion and other operational trauma or wear. This may lead one or more components in a machine to develop a damage state, such as crack formation in the body or coatings of the component. Operation of a rotating machine creates vibrations within the machine and its components. All mechanical components possess a resonance frequency that creates greater oscillation under such excitation at a specific preferential frequency. When a weakened component reaches the resonance frequency, this state will often lead to cracking. This initial damage state under normal service condition, may be difficult to detect from convention AE signal-based health monitoring systems. However, once cracking occurs, the resonance frequency of the damaged component changes and it will detune from the normal service conditions frequency, lowering the resonance frequency and bringing it within the operating range of the machine during startup and shutdown of the machine from its normal service conditions. Crossing the resonance frequency of the damage state of the component creates additional excitation events which at least lead to rubbing of the adjacent sides of the cracks and can often trigger crack propagation. Because of this, startup and shutdown of the machine operate as a frequency sweep for detecting the resonance frequencies of damaged components within the system. In conjunction with a system for detecting and analyzing AE signals that include features representative of excitation events in the components, resonance detection can be used to identify and monitor damaged components. More specifically, characterizing the amplitude, shape, and change in resonance frequency from one event to the next can enable a predictive model of component wear and failure conditions for improved monitoring, including calculation of crack growth rate, and more accurate remedial action.

Figure 1:
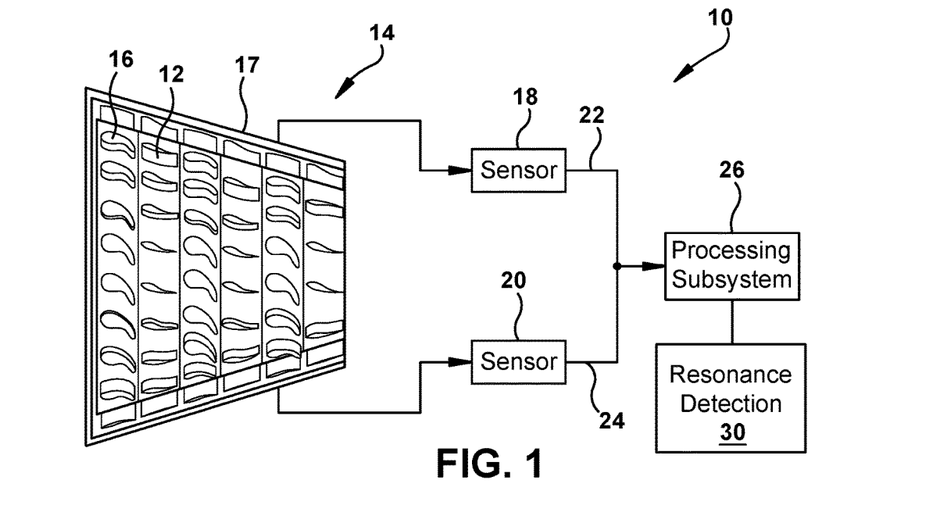
FIG. 1 shows a diagram of an example system for monitoring the health of a component in a machine using resonance detection.

FIG. 1 shows a diagram of an example system 10 for monitoring the health of a component, such as stator vanes 12, in a machine, such as axial compressor 14, using resonance detection 30. Monitoring the health of the stator vanes 12, for example, includes identifying the occurrence of cracking in the stator vanes 12. In one embodiment, monitoring the health of the stator vanes 12 includes modeling crack length and tracking crack propagation over time based on changes to the resonance frequency of the stator vanes 12. Modeling crack length and tracking crack propagation over time may enable the system 10 to determine the remaining useful life of the stator vanes 12 and set thresholds or triggers for inspection, repair, or decommissioning of the machine. It is noted that while the present systems and methods may be used for monitoring the health of stator vanes, the present methods and systems may be used for monitoring the health of stationary blades and other machine components subject to damage states that change their resonant frequencies. It is also noted that while the present systems and methods are shown with regard to stator vanes 12 in an axial compressor 14, the present methods and systems may be used for monitoring the health of components in other machines, including various turbomachines, compressors, gas turbines, steam turbines, or generators.

In the example shown in FIG. 1, the axial compressor 14 includes a plurality of rows of rotating blades 16 and the plurality of rows of stator vanes 12. Each of the rows of rotating blades 16 is located alternately with respect to each of the rows of stator vanes 12, and vice versa. The system 10 further includes a plurality of sensing devices 18, 20 that are dispersed on the outer surface of a casing 17 that covers the rows of rotating blades 16 and the rows of stator vanes 12. The sensing devices 18, 20 may include magnetostrictive material sensing devices, piezoelectric sensing devices, capacitive sensing devices, or other sensing devices that convert acoustic waves to electrical signals, such as acoustic emissions (AE) signals 22, 24. The sensing devices 18, 20 for example, may also include optical sensing devices, acoustic emission sensing devices, radio frequency wireless sensing devices, or similar sensor packages that are capable of converting acoustic waves to electrical signals that can be used by system 10.

Though the present system 10 shows two sensing devices 18, 20, the system 10 may include an optimal number of sensing devices based upon the size of the axial compressor 14 and precision expected in monitoring the stator vanes 12. The location of the sensing devices 18, 20 on the outer surface of the casing 17 is determined using triangulation techniques. The triangulation techniques assist in identifying optimal locations for the sensing devices 18, 20. Optimal locations for the sensing devices are locations for distribution of the sensing devices in the outer surface of the machine such that AE waves generated by each component being monitored are captured by the sensing devices and enable the use of signal processing to associate specific AE signals or portions of AE signals with specific components being monitored (through triangulation or similar techniques).

When one or more of the stator vanes 12 are operating under stress or under uncharacteristic operating conditions, including their respective resonance frequencies, they generate AE waves. The AE waves travel through different interfaces between the stator vanes and the casing 17 to reach the outer surface of the casing 17. These AE waves reach the outer surface of the casing, the sensing devices 18, 20 measure the AE waves to generate the AE signals 22, 24. Each of the AE signals 22, 24 is a time-series signal in voltage. The sensing device 18 generates the AE signals 22 and the sensing device 20 generates the AE signals 24. The frequency range of the AE signals 22, 24 typically vary from about 50 kHz to about 1000 kHz.

The system 10 further includes a processing subsystem 26 that receives the AE signals 22, 24 from the sensing devices 18, 20. The processing subsystem 26 may include various components, such as microprocessors, coprocessors, memory/media elements for data storage, software instructions, wired/wireless communication channels, user interfaces, and other data processing components. The various memory/media elements for data storage, including storage of software executables, may be one or more varieties of computer readable media, such as, but not limited to, any combination of volatile memory (e.g., RAM, DRAM, SRAM, etc.), non-volatile memory (e.g., solid state drives, hard drives, optical media, magnetic tapes, etc.), and or other memory types. Any possible variation of data storage and processing configurations, including mass market computing devices (e.g., personal computers, laptops, tablets, smartphones, etc.) running appropriate software applications, will be appreciated by one of ordinary skill in the art.

In the presently contemplated configuration, the processing subsystem 26 receives the AE signals 22, 24. In certain embodiments, the AE signals 22, 24 may be preprocessed by intermediate devices before reaching the processing subsystem 26. For example, the intermediate device may include an amplifier, an interface unit, a data acquisition system, and the like. The preprocessing may increase the strength and quality of the AE signals 22, 24 before they are received by the processing subsystem 26. In some embodiments, preprocessing may include conversion from analog electrical AE signals to digital AE signals and/or integration and separation of AE signals into AE signals directly correlating to specific components. An embodiment of the present systems and techniques where the AE signals 22, 24 are preprocessed before reaching the processing subsystem 26 is explained with reference to FIG. 2.

The processing subsystem receives the AE signals 22, 24 from the sensing devices 18, 20 in real-time during operation of the axial compressor 14. The processing subsystem 26 processes the AE signals 22, 24 to monitor the health of the stator vanes 12. In one embodiment, the processing subsystem is remotely located with respect to the location of the axial compressor 14 and may remotely monitor the health of the stator vanes 12 in real-time without human interference. Therefore, the processing subsystem 26 may automatically monitor the health of the stator vanes 12 in real-time. In another embodiment, the processing subsystems 26 may be located in the vicinity of the axial compressor 14.

The processing of the AE signals 22, 24 enables the processing subsystem 26 to identify specific stator vanes 12 and then determine features or events in the AE signals 22, 24 that are analyzed for information regarding the health of the stator vanes 12 and axial compressor 14. In one embodiment, the features, for example, include time-domain features and frequency-domain features. For example, the time-domain features include ring down count (RDC), amplitude, event duration (ED), peak amplitude (PA), rise time (RT), energy, or the like. Ring down count may refer to a number of times an AE signal crosses a dynamic threshold. Event duration may refer to a duration between a first time instance an AE signal crosses a dynamic threshold and a second time instance when the AE signal crosses the dynamic threshold. Rise time may refer to the time taken by an AE signal from a first crossing of a dynamic threshold to its peak amplitude in a given waveform. The frequency domain features, for example, may include frequency distribution of the power spectral density of the AE signals, the variations in these distributions, wavelets, and the like. Determination of features enables analysis of the features. An AE signals feature associated with time information may be referred to as an event in the AE signals.

In the example embodiment shown, the processing subsystem 26 includes or interfaces with a resonance detection system 30. The resonance detection system 30 uses the AE signals 22, 24 and/or features or events therefrom to detect a resonance frequency of the stator vanes 12 and, more specifically, changes in the resonance frequency of the stator vanes 12 based upon damage states, such as cracks. The resonance detection system 30 thereby assists the processing subsystem 26 in monitoring the health of the stator vanes 12.

Figure 2:
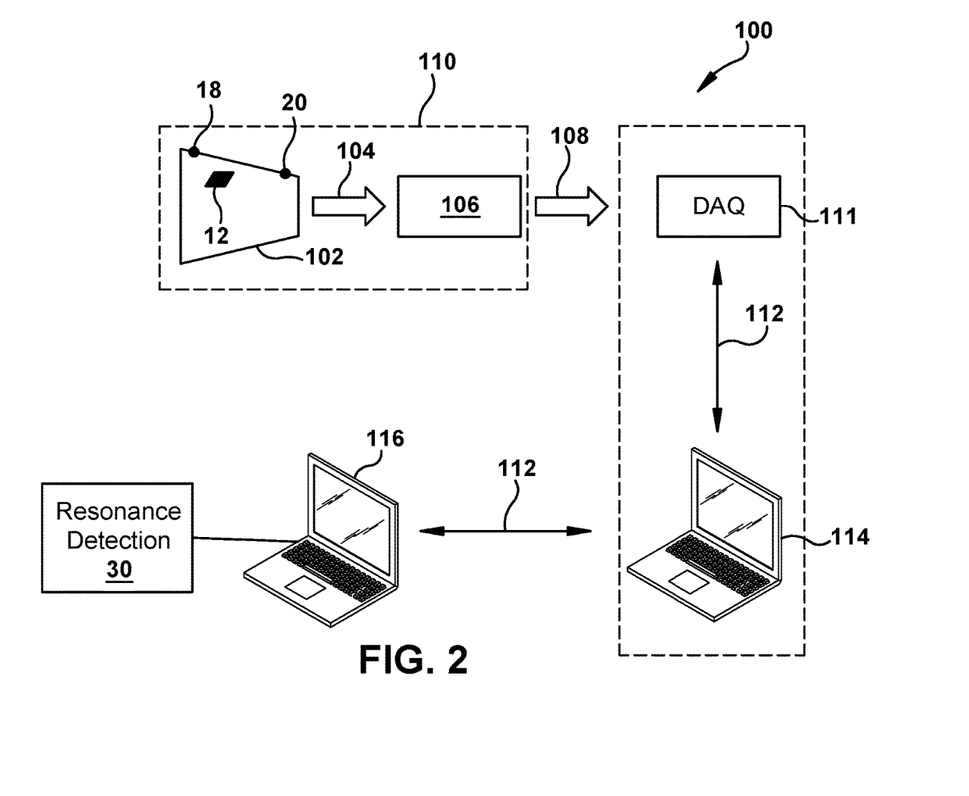
FIG. 2 shows a diagram of another example system for monitoring the health of a component in a machine using resonance detection.

FIG. 2 is a diagram of an example system 100 for monitoring the health of a component, such as stator vanes 12, in a machine, such as a compressor 102, using resonance detection according to another embodiment of the invention. The system 100 illustrates preprocessing of AE signals by intermediate devices before the AE signals reach a processing subsystem. The system 100 includes a plurality of sensing devices 18, 20 that are mounted on the outer surface of a casing of a compressor 102. The sensing devices 18, 20 generate AE signals 104 that are representative of stress waves in at least one of the stator vanes 12 in the compressor 102. The sensing devices 18, 20 are physically coupled with an amplification device 106. The amplification device 106 is located in a turbine compartment 110 of the compressor 102. In alternative embodiments, the amplification device 106 may be located outside the turbine compartment 110. The amplification device 106 may be physically coupled with the sensing devices 18, 20 via high temperature cables. The amplification device 106 amplifies the AE signals 104 to improve the strength of the AE signals 104. Consequent to the amplification of the AE signals 104, amplified AE signals 108 are generated.

The system 100, further includes a data acquisition system (DAQ) 111. The DAQ 111 is operationally coupled with the amplification device 106. The DAQ 111 receives the amplified AE signals 108 and converts the amplified AE signals 108 into digital AE signals 112. In one embodiment, the DAQ 111 may remove noise from the amplified AE signals 108 before converting them into digital AE signals. The system 100 further includes a first processing subsystem 114. The first processing subsystem 114 may be operationally associated with the DAQ 111. In some embodiments, the first processing subsystem 114 is located in the vicinity of the DAQ 111. In another embodiment, the DAQ 111 may be a part of the first processing subsystem 114. In alternative embodiments, the first processing subsystem 114 may perform the functions of the DAQ 111 based on receiving the amplified AE signals directly from the amplification device 106 and the system 100 may operate without a separate DAQ.

The first processing subsystem 114 receives the digital AE signal 112 from the DAQ 111 in the form of a digital AE data in a real-time stream, near real-time batches, or other periodic transfers of AE data with associated timing information. The first processing subsystem 114 processes the digital AE signals 112 to determine features corresponding to the AE data. Subsequently, the first processing subsystem 114 analyzes the features to monitor the health of the stator vanes 12. The system 100 further includes a second processing subsystem 116 that is located at a remote location with respect to the locations of the compressor 102 and the first processing subsystem 114. The second processing subsystem 116 is operatively associated with the first processing subsystem 114 via a wired or wireless communication medium, such as a wireless internet connection.

The second processing subsystem 116 is configured to enable a user to access the first processing subsystem 114. Therefore, the second processing subsystem may be used by a user to monitor the health of the stator vanes 12 from a remote location. Particularly, the second processing subsystem 116 enables a user to review monitoring results and intermediate processing results, and results related to analysis of features generated by the first processing subsystem 114. In the example shown, the second processing subsystem 116 is associated with the resonance detection system 30, enabling the second processing subsystem 116 to perform additional analysis of features related to the resonance frequency of stator vanes 12 based on digital AE signals 112 that the first processing subsystem 114 may not be capable of In one embodiment, the second processing subsystem 116 selectively accesses digital AE signals 112 stored as AE data on the first processing subsystem 114.

Figure 3:
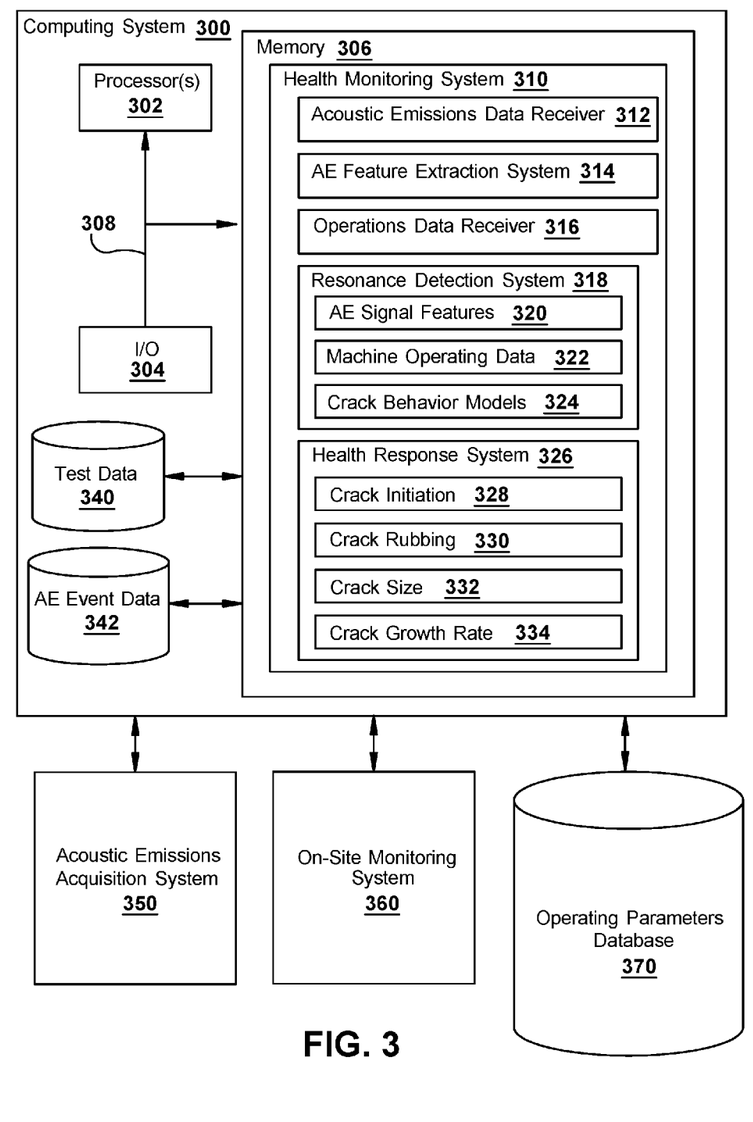
FIG. 3 shows a diagram of another example system for monitoring the health of a component in a machine using resonance detection.

FIG. 3 shows an example computing system 300 such as may be used as a processing subsystem in the embodiments of FIG. 1 and FIG. 2 for monitoring the health of components in a machine using resonance detection. Computing system 300 includes processor(s) 302, input/output devices (I/O) 304, and memory 306 interconnected by a communication bus 308. As described above with regard to processing subsystem 26 in FIG. 1, those of ordinary skill in the art will appreciate the many combinations of conventional computer system components that may be used to implement computing system 300.

The health monitoring system 310 instantiated in the memory 306 enables monitoring the health of one or more components in one or more machines based on AE signals received by the computing system 300. In one embodiment, the health monitoring system 310 and its components are implemented in one or more executable software applications and related runtime environments and data structures. While the health monitoring system 310 is shown in the context of a single computing device 300, those of ordinary skill in the art will understand that its functions may be split across multiple computing devices, as described above for certain embodiments of the first processing subsystem 114 and the second processing subsystem 116 in FIG. 2. In one embodiment, some or all functions of the health monitoring system 310 are components of a general machine health monitoring software package, while some functions may be part of another software package or extension specifically for addressing the use of resonance detection in monitoring the health of machine components.

The acoustic emissions (AE) data receiver 312 receives AE signals from a plurality of sensing devices that collect AE signals from a machine, where the AE signals correspond to specific components within the machine. The AE signals are representative of acoustic emission waves propagating through the components of the machine. The AE signals may be received as digital AE data providing amplitude, time, and frequency information. More specifically, the AE data receiver 312 may receive AE signals from an acoustic emissions (AE) acquisition system 350, such as the sensing devices and preprocessors described above with regard to FIG. 1 and FIG. 2. In some embodiments, the AE signals received will represent a plurality of sensing devices detecting the acoustic emission waves of a plurality of machine components and the AE data receiver 312 will process the AE signals to separate the AE signal components that relate to specific components by location using triangulation or similar techniques. The AE signal related to a specific and locatable machine component can then be further processed and analyzed by other functions in the health monitoring system 310. The received AE signal may include features that represent resonance frequency excitation events in components having a damage state that has brought their resonance frequency within the operating frequency of the machine, particularly during startup and shutdown.

The AE feature extraction system 314 analyzes the received AE signals from the AE data receiver 312 to identify features of interest within the AE signal. Analysis of the AE signals may include both time domain and frequency domain features as described above with regard to processing subsystem 26 in FIG. 1. The features extracted by AE feature extraction system 314 are communicated to the resonance detection system 318 for detecting and characterizing resonance frequency crossing events for components in a damage state.

The health monitoring system 310 may also include an operations data receiver 316 for receiving information regarding the operational condition of the machine from another data source, such as an on-site monitoring system 360 that collects and organizes an array of specifications and operational information regarding the general operations and performance of the machine. For example, the on-site monitoring system 360 may include information regarding the operational state of the machine, including startup, normal service, and shutdown conditions, performance and duty cycles of the machine, operating and repair histories, as well as physical specifications for the machine and its components. Some or all of this information may be stored in an operating parameters database 370 relevant to the machine and components. Any of this information may be accessed and used by the resonance detection system 318 and/or the health response system 326 to improve the models and response thresholds for the health monitoring system 310.

The resonance detection system 318 identifies the resonance frequency of the damage state during operation of the machine using the AE signals and analyzes the AE signal features proximate the resonance frequency to assist in characterizing the damage state. The resonance detection system 318 includes a plurality of AE signal features 320, machine operating data 322, and crack behavior models 324 known to be identified with resonance frequency events. Test data 340, based on characterization of damage related resonance frequency events in similar systems (potentially including both lab testing and data collected from operating systems in the field), may be used to define the AE signal features 320, machine operating data 322, and crack behavior models 324 in terms of relevant parameters that can be used to analyze the incoming AE signal features for a particular machine and components. Once a resonance frequency event is detected in the AE signal, its amplitude, duration, rise time, and other relevant characteristics of the AE signal proximate the resonance frequency event can be stored in AE event data 342 and communicated to the health response system 326. Proximate the resonance frequency means between a first time instance the AE signal crosses a dynamic threshold signifying the beginning of the resonance frequency event and a second time instance when the AE signal crosses the dynamic threshold signifying the end of the resonance frequency event. A resonance frequency event may be described by the dynamic threshold signaling the beginning and ending of the event relative to the AE signal baseline, the maximum amplitude, and the respective timing information for the first time instance, maximum amplitude, and second time instance.

The health response system 326 analyzes each resonance frequency event from the AE signals and aggregates information on resonance frequency events over time in order to characterize and monitor the damage state and trigger appropriate responses. The health response system 326 includes parameters for identifying a crack initiation event 328, where a new damage state is first discovered in a component. Ideally, this can be detected from analysis of the AE signal during normal service conditions when the wear condition of the component first reaches resonance frequency and initiates cracking and detuning of the resonance frequency. In some embodiments and instances, it may not be detected until the resonance frequency has already detuned sufficiently to appear in the startup or shutdown frequency ranges. The health response system 326 includes parameters for identifying a crack rubbing event 330, where the rubbing of the existing crack surfaces due to twisting of the component during a resonance frequency event generates the AE signal, but no further cracking occurs. Crack rubbing events 330 may be important for monitoring the health of a damaged component by providing insight that such a component can be monitored without further response as long as the number of cycles and mechanical energy imparted to the component continues to be too low to cause further cracking in the component. The health response system 326 includes parameters for estimating crack size 332, where the amplitude of the resonance frequency event, operating speed of the machine, and component specifications and crack behavior models 324 may be used to estimate the crack size. The health response system 326 includes parameters for estimating crack growth 334, where the characteristics of resonance frequency events for a component are compared across time to calculate the rate of growth. More specifically, the strength of the AE events, the rate at which the component is detuning and the resonance frequency moves from one event to the next provides a measure of the rate of change. Similarly, monitoring the rate of change across more resonance frequency events may demonstrate that the rate of change is increasing or decreasing, further enabling the health response system 326 to predict changes in the damage state and set reasonable thresholds for actions such as inspection, repair, emergency shut down, and/or decommissioning. The purpose of the health response system 326 includes both monitoring to enable a user to check the status of components with damage states and setting thresholds for action by estimating time to failure or liberation and/or raising an alarm if crack length estimate or crack growth rate reach critical levels. Further, characterization and monitoring of the damage states and how operating conditions excite resonance in the damaged components enables technicians or an emergency response system to shut down the machine in such a way that it is less likely to further damage the component.

Figure 4:
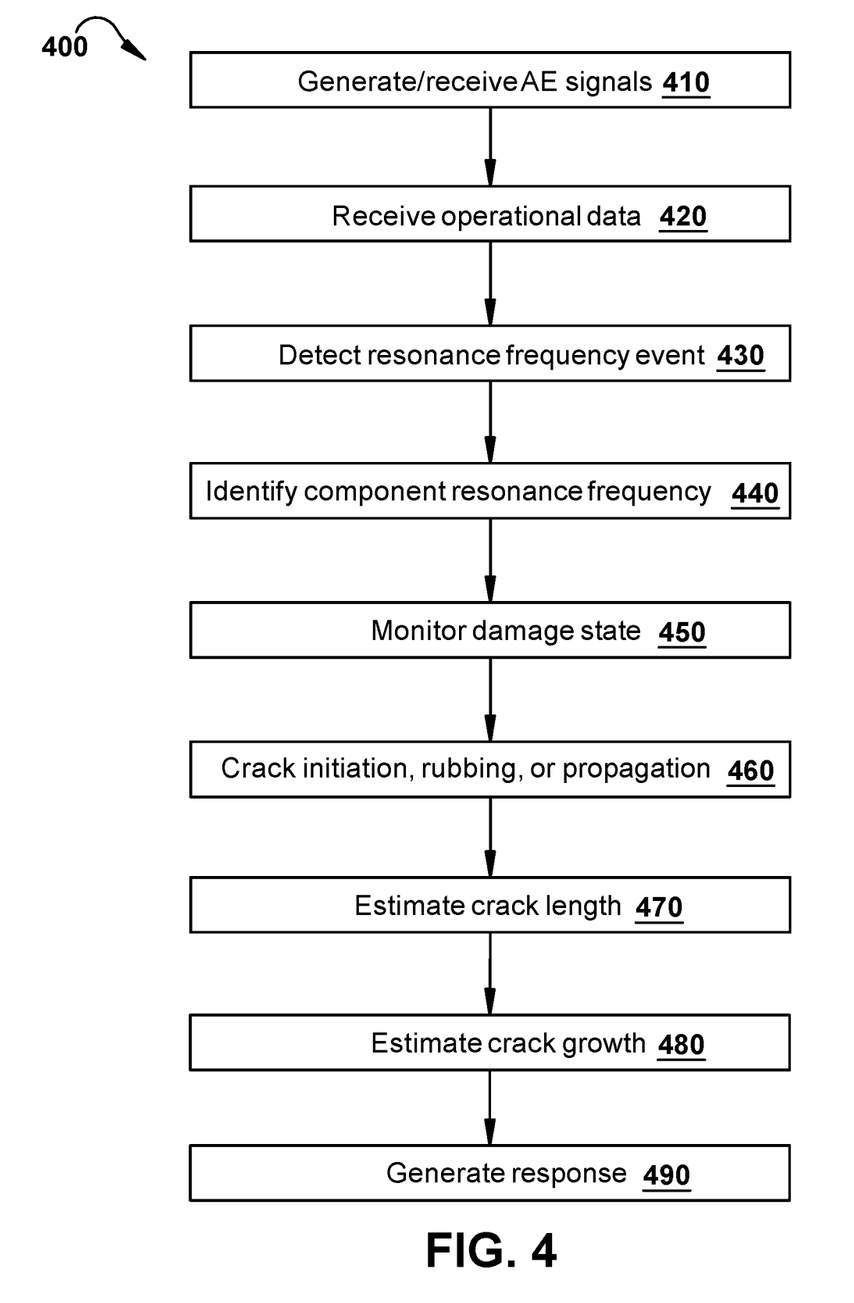
FIG. 4 shows an example flow diagram of a method for monitoring the health of a component in a machine using resonance detection.

FIG. 4 is an example flow diagram of a method 400 for monitoring the health of a component in a machine using resonance detection, such as may be used with systems 10 in FIG. 1, 100 in FIG. 2, or 300 in FIG. 3. The method 400 is a single example and those of ordinary skill in the art will appreciate the versatility of the described systems and, specifically, how the order and details of the example method 400 are not limiting to the capabilities or desired uses of the above described systems. In step 410, AE signals that are representative of acoustic emission waves propagating through a component of a machine are received. In step 420, operational data regarding the operating conditions of the machine are received. In step 430, a resonance frequency event is detected from the AE signals that represent a damage state in the component. In step 440, the resonance frequency of the damage state of the component is identified from the resonance frequency event, along with other AE signal features of the resonance frequency event. In step 450, features of the resonance frequency event and data regarding the operating conditions of the machine are used to characterize and monitor the damage state based on the AE signal proximate the resonance frequency. In step 460, crack initiation, rubbing, or propagation are distinguished from one another. In step 470, crack length is estimated. In step 480, crack growth is estimated. In step 490, a response is generated based upon the damage state and/or predictive value of the characterization of the resonance frequency event(s).

Figure 5:
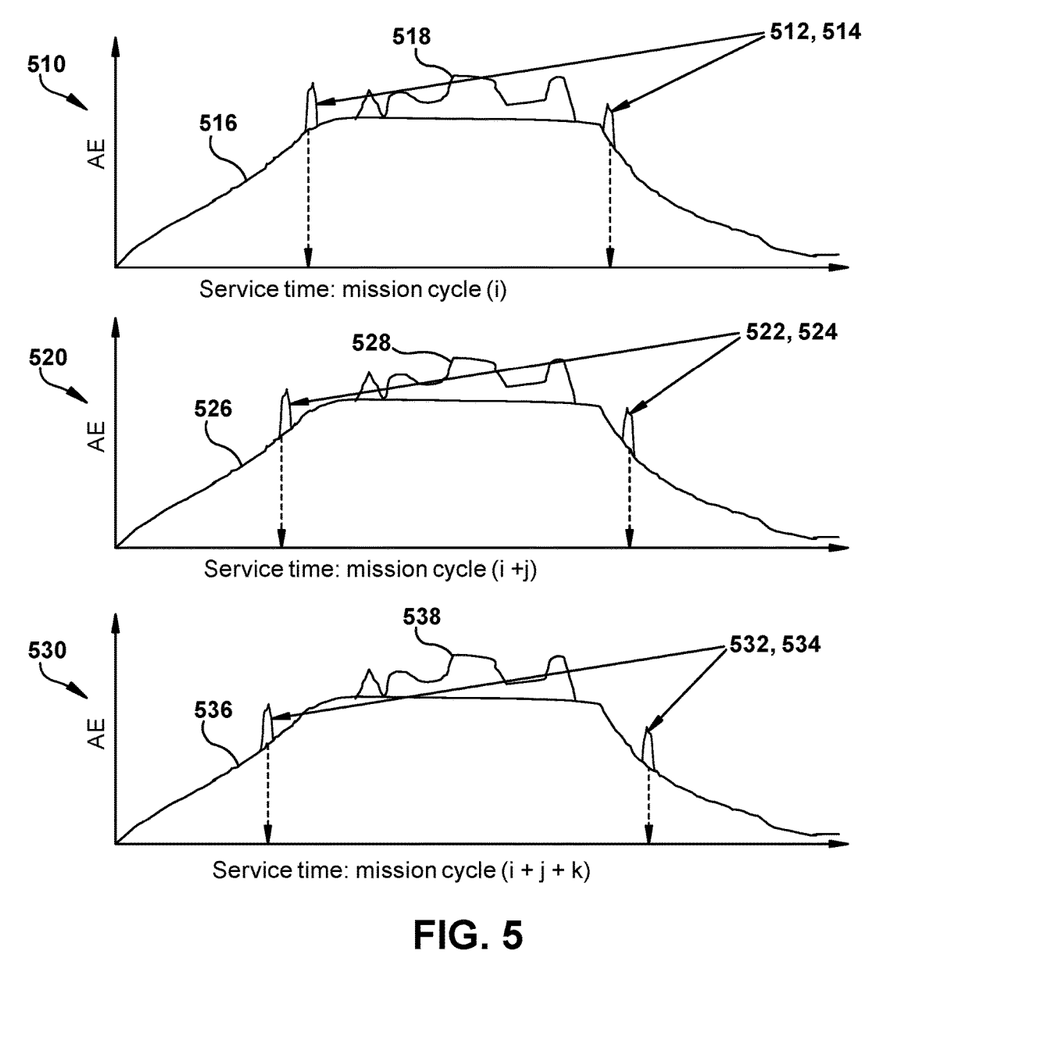
FIG. 5 shows an example graph of acoustic emissions signals with damage related AE events or features.

FIG. 5 is a series of example graphs 510, 520, 530 of acoustic emissions signals with damage related AE events or features showing the detuning of resonance frequency events over time and mission cycle. A typical mission cycle consists of startup (ramping up of signal), normal service condition (plateau region), and shutdown (ramping down of signal). Graph 510 shows the AE signal graph for a given component at mission cycle (i), a first time point, showing two resonance frequency events 512, 514 related to crossing the resonance frequency of a damage state, once during startup and once during shutdown. Graph 510 shows a baseline AE signal 516 and other AE signal features 518 occurring during normal service conditions and unrelated to the two resonance frequency events 512, 514. In this example, the damage state represents a cracked component that is cracking further each occurrence and detuning with each event 512, 514, 522, 524, 532, 534, causing the resonance frequency of the damaged component to move further from the normal service conditions into the startup and shutdown portions of the mission cycle. Graph 520 shows the AE signal graph for the same component at mission cycle (i+j), a second time point, showing two resonance frequency events 522, 524 related to crossing the resonance frequency of a damage state. Graph 520 shows a baseline AE signal 526 and other AE signal features 528 occurring during normal service conditions and unrelated to the two resonance frequency events 522, 524. Graph 530 shows the AE signal graph for the same component at mission cycle (i+j+k), a third time point, showing two resonance frequency events 532, 534 related to crossing the resonance frequency of a damage state. Graph 530 shows a baseline AE signal 536 and other AE signal features 538 occurring during normal service conditions and unrelated to the two resonance frequency events 512, 514.

Figure 6A:
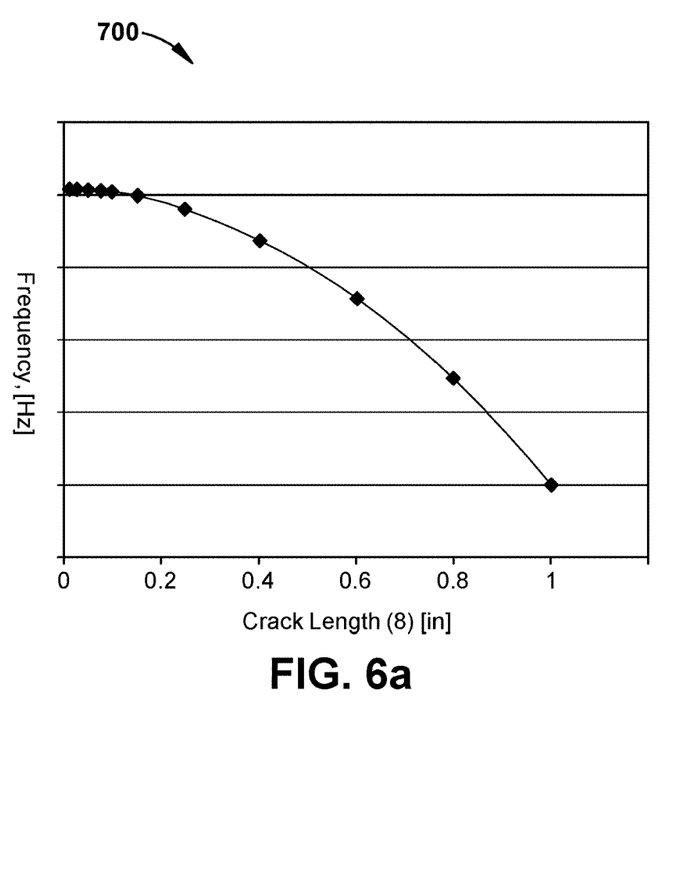
FIG. 6a shows an example graph of resonance frequency versus crack length in a component.
Figure 6B:
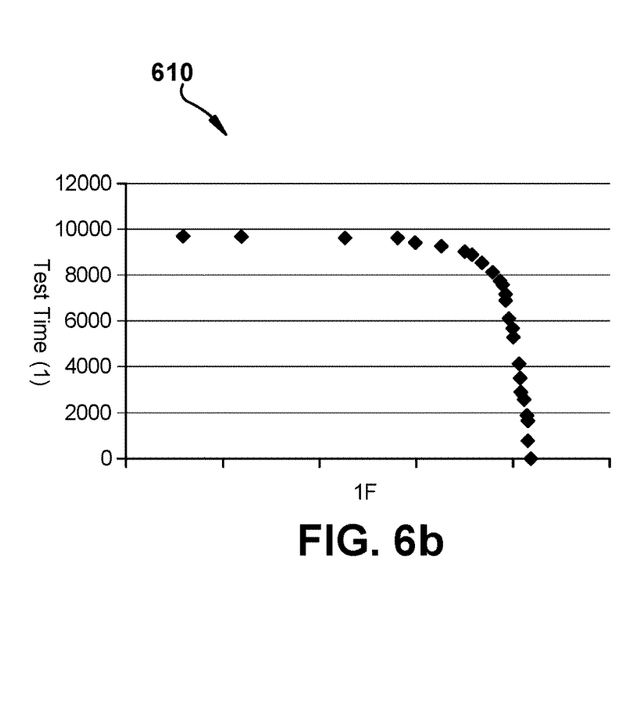
FIG. 6b shows an example graph of test time versus resonance frequency.
Figure 6C:
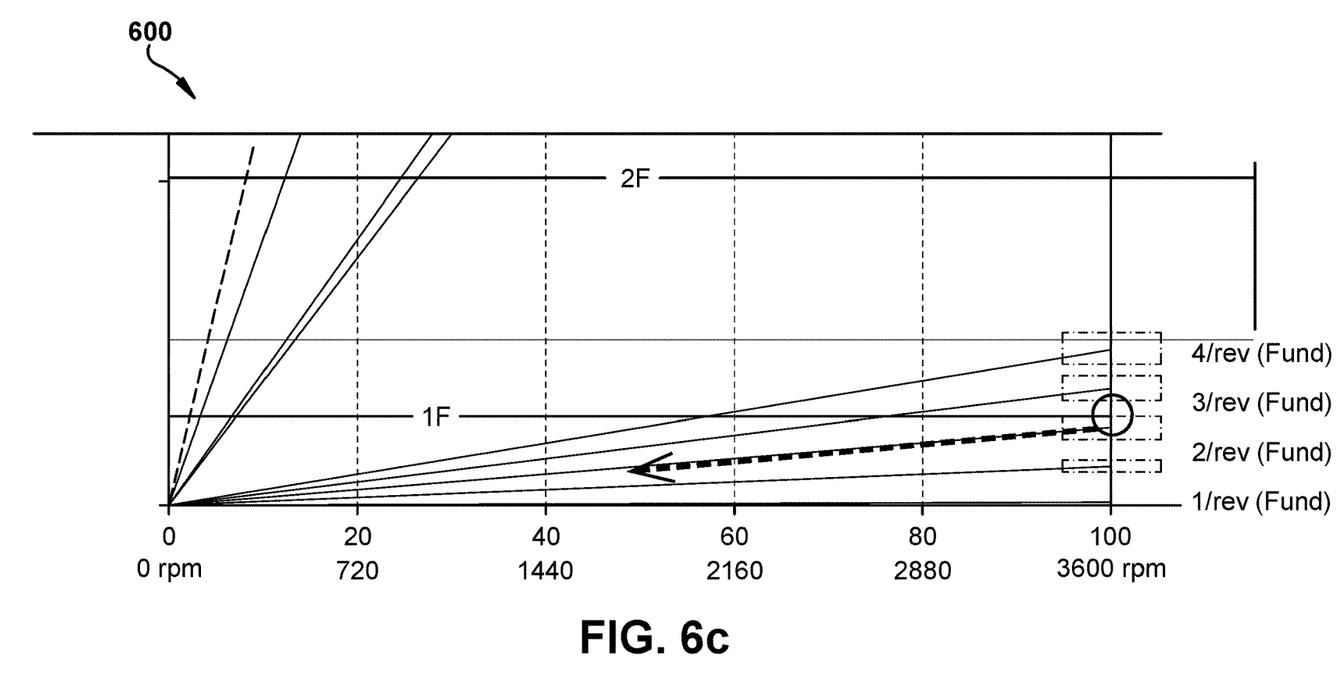
FIG. 6c shows an example Campbell diagram for a machine with component resonance frequencies changing over time due to an increasing damage state.

FIG. 6 includes a number of example plots for a machine with component resonance frequencies changing over time due to a damage state. Graph 700 in FIG. 6*a* is an example of resonance frequency changes versus crack length in a component to demonstrate how crack length can be estimated from resonance frequency events. Graph 610 in FIG. 6*b* is an example of resonance events versus test time further demonstrating changes in resonance frequency over time as the damage state of a component increases. FIG. 6c is an example Campbell diagram 600 for a machine with component resonance frequencies changing over time due to a damage state. Graph 610 shows the curve representing these changes.

Figure 7:
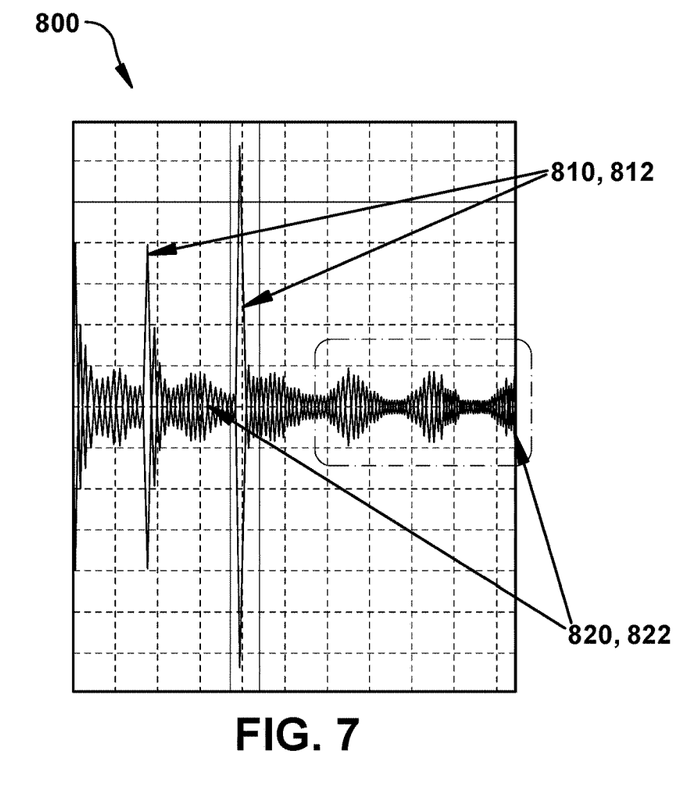
FIG. 7 shows an example graph of an AE signal with events or features related to cracking and rubbing.

FIG. 7 is an example graph 800 of an AE signal with events or features related to cracking and rubbing. Resonance frequency events 810, 812 have fast rise times, short durations, and higher maximum amplitudes characterizing a cracking event. Resonance frequency events 820, 822 have much slower rise times, longer durations, and lower maximum amplitudes characterizing a rubbing event.

Figure 8:
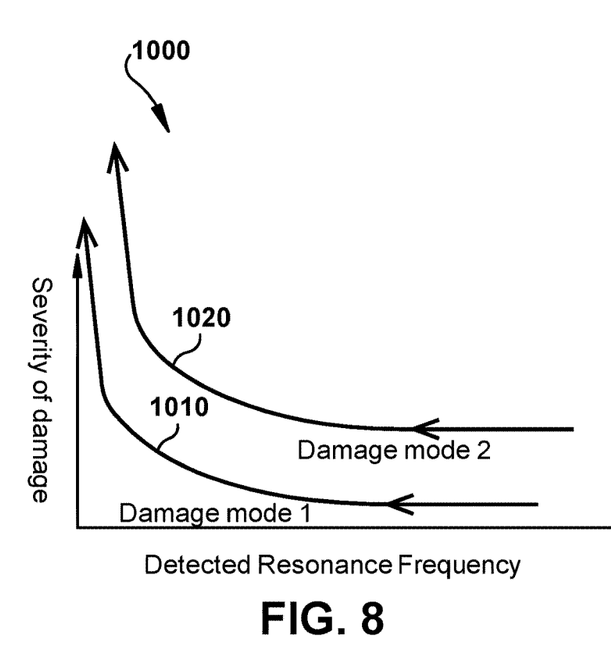
FIG. 8 shows an example graph of severity of damage versus detected resonance frequency.

FIG. 8 is an example graph 1000 showing severity of damage versus detected resonance frequency changes or detuning. This can be related to turbine speed using Campbell diagrams (FIG. 6c). In FIG. 8, two representative damage modes 1010, 1020 are shown. In principle, there might be one or more such modes of damage either from the same component or across different components.

The foregoing drawings show some of the operational processing associated according to several embodiments of this disclosure. It should be noted that in some alternative implementations, the acts described may occur out of the order described or may in fact be executed substantially concurrently or in the reverse order, depending upon the act involved.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A system comprising:
a plurality of sensing devices configured to generate acoustic emission (AE) signals that are representative of acoustic emission waves propagating through at least one component of a machine, wherein the at least one component has a damage state and the damage state has a resonance frequency; and
a processing subsystem that is in operational communication with the plurality of sensing devices to receive AE signals, wherein the processing subsystem includes a resonance detection system that identifies the resonance frequency of the damage state during operation of the machine using the AE signals;
wherein the processing subsystem monitors the damage state of the at least one component using the resonance detection system; and
wherein the resonance frequency of the damage state of the at least one component changes over time and the processing subsystem monitors the magnitude of the AE signals proximate the resonance frequency and the change in the resonance frequency over time to determine risk to health of the at least one component.

2. The system of claim 1, wherein the processing subsystem is configured to monitor health of a plurality of components by location during real-time operation of the machine, the plurality of components including the at least one component.

3. The system of claim 1, wherein the at least one component is a stator vane.

4. The system of claim 1, wherein the machine is selected from a compressor, a gas turbine, a steam turbine, and a generator.

5. The system of claim 1, wherein the resonance frequency of the damage state is detected during a change in an operational state of the machine that causes an excitation in the component at the resonance frequency of the damage state and creates a detectable event in the AE signals.

6. The system of claim 5, wherein the resonance detection system operates during a start-up operation and a shutdown operation of the machine.

7. The system of claim 1, wherein the AE signals proximate the resonance frequency of the damage state are associated with rubbing of crack faces and the resonance detection system distinguishes rubbing of crack faces from crack propagation.

8. The system of claim 7, wherein the resonance detection system uses a rise time value and an amplitude value of the AE signals proximate the resonance frequency to distinguish rubbing of crack faces from crack propagation.

9. The system of claim 1, wherein the resonance detection system comprises a plurality of crack detection algorithms based on AE signal features, machine operating data, and models of crack behavior.

10. A method of monitoring the health of a component of a machine, the method comprising:
generating acoustic emission (AE) signals that are representative of acoustic emission waves propagating through at least one component of the machine, wherein the at least one component has a damage state and the damage state has a resonance frequency;
identifying the resonance frequency of the damage state during operation of the machine using received AE signals; and
monitoring the damage state of the at least one component using the received AE signals proximate the resonance frequency of the damage state, wherein the resonance frequency of the damage state of the at least one component changes over time and the monitoring of the damage state comprises monitoring the magnitude of the AE signals proximate the resonance frequency and the change in the resonance frequency over time to determine risk to health of the at least one component.

11. The method of claim 10, wherein monitoring the damage state further comprises monitoring the health of a plurality of components by location during real-time operation of the machine, the plurality of components including the at least one component.

12. The method of claim 10, wherein the at least one component is a stator vane.

13. The method of claim 10, wherein the machine is selected from a compressor, a gas turbine, a steam turbine, and a generator.

14. The method of claim 10, wherein the resonance frequency of the damage state is identified during a change in an operational state of the machine that causes an excitation in the component at the resonance frequency of the damage state and creates a detectable event in the received AE signals.

15. The method of claim 14, wherein monitoring the damage state operates during a start-up operation and a shutdown operation of the machine.

16. The method of claim 10, wherein the received AE signals proximate the resonance frequency of the damage state are associated with rubbing of crack faces and the monitoring of the damage state distinguishes rubbing of crack faces from crack propagation.

17. The method of claim 16, wherein the monitoring of the damage state uses a rise time value and an amplitude value of the received AE signals proximate the resonance frequency to distinguish rubbing of crack faces from crack propagation.

18. The method of claim 10, wherein identifying the resonance frequency comprises a plurality of crack detection algorithms based on AE signal features, machine operating data, and models of crack behavior.

19. A system for monitoring component health of a machine, comprising:

an acoustic emission (AE) data receiver for receiving AE signals that are representative of acoustic emission waves propagating through at least one component of the machine, wherein the at least one component has a damage state and the damage state has a resonance frequency;

a resonance detection system for identifying the resonance frequency of the damage state during operation of the machine using the AE signals; and a health response system for monitoring the damage state of the at least one component using the AE signals proximate the resonance frequency of the damage state, wherein the health response system uses the magnitude of the AE signals proximate the resonance frequency and the change in the resonance frequency over time to calculate a crack growth rate and the crack growth rate is used to generate the response to the detected risk to health of the at least one component.

20. The system of claim 19, further comprising an AE feature extraction system and an operations data receiver used by the resonance detection system for identifying the resonance frequency of the damage state.

21. The system of claim 19, wherein the health response system uses the magnitude of the AE signals proximate the resonance frequency and the change in the resonance frequency over time to calculate a crack growth rate and the crack growth rate is used to generate the response to the detected risk to health of the at least one component.

* * * * *